United States Patent [19]

Melin

[11] 4,402,942
[45] Sep. 6, 1983

[54] OXYTOCIN DERIVATIVES

[75] Inventor: Per O. R. Melin, Malmö, Sweden

[73] Assignee: Ferring AB, Malmö, Sweden

[21] Appl. No.: 238,715

[22] Filed: Feb. 27, 1981

[30] Foreign Application Priority Data

Mar. 24, 1980 [SE] Sweden ............................ 8002222

[51] Int. Cl.³ ..................... A61K 37/00; C07C 103/52
[52] U.S. Cl. .............................. 424/177; 260/112.5 R
[58] Field of Search .................. 424/177; 260/112.5 R

[56] References Cited

PUBLICATIONS

I. Krejei, et al., Chem. Abstr., vol. 67, (1967), 97363p.
Bankowski, et al., J. Med. Chem., (1978), vol. 21, 850-853.
Karl Jost, et al., Chem. Abstr., 79, (1973), 137506v.
Taira Norio, et al., Chem. Abstr., 67, (1967), 8386j.
Collection Czechoslov. Chem. Commun., vol. 36, (1971).
Nature, 218, (1968), 197-199.
Collection Czechoslov. Chem. Commun., 34, (1969), 2848-2852.
Collection Czechoslov. Chem. Commun., 39, (1974), 1290-1302.

Primary Examiner—Delbert R. Phillips
Attorney, Agent, or Firm—Beveridge, DeGrandi & Kline

[57] ABSTRACT

New oxytocin derivatives having an inhibitory effect on uterine contractions, pharmaceutical compositions containing the oxytocin derivatives, and use of the derivatives in the production of medicines are described. The derivatives are 1-deamino-(2-O-alkyltyrosine)-oxytocin of the formula Mpa—Tyr(X)—Ile—Gln—Asn—Cys—Pro—Leu—Gly—NH₂
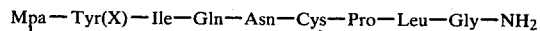

wherein Mpa is a 3-mercaptopropionyl residue and X is an alkyl group having 2-4 carbon atoms, preferably an ethyl group. Apart from their inhibitory effect on vasopressin and oxytocin induced uterine contractions, the new oxytocin derivatives are capable of inhibiting the spontaneous contraction pattern of the uterus.

14 Claims, No Drawings

OXYTOCIN DERIVATIVES

This invention relates to new oxytocin derivatives, viz. 1-deamino-(2-O-alkyl-tyrosine)-oxytocin, which have an inhibitory effect on uterine contractions. More particularly, these new oxytocin derivatives have an inhibitory effect on vasopressin and oxytocin induced uterine contractions in vitro and in vivo (human and rat) and also on the spontaneous contraction pattern of the uterus.

The oxytocin derivatives according to the invention differ from the natural hormone oxytocin in that the hydrogen in the hydroxyl group of the tyrosine is substituted with alkyl and that the cysteine at position 1 is deaminated. Thus the oxytocin derivatives concerned have the formula:

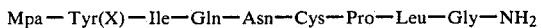

wherein Mpa is a 3-mercaptopropionyl residue (—S—CH$_2$—CH$_2$—CO—) and X is an alkyl group which substitutes the hydrogen in the hydroxyl group

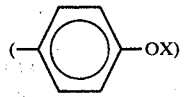

of the tyrosine, in which case X is a lower alkyl group having 2–4 carbon atoms, preferably ethyl. The alkyl group can thus be ethyl, propyl or butyl. Alkyl groups having 5 or 6 carbon atoms are also conceivable, but they presumably reduce the inhibition.

The following structurally closely related oxytocin derivatives are described and said to have an antagonistic effect on oxytocin induced uterine contractions: 2-O-methyltyrosine-oxytocin and 2-O-ethyltyrosine-oxytocin (Rudinger, J. & Krejci, I. Antagonists of the Neurohypophysical Hormones. Handbook of Experimental Pharmacology, Vol. 23, (1968) pp 748–801. Ed. B. Berde, Berlin, Heidelberg & New York: Springer Verlag), N$^\alpha$-acetyl-2-O-methyltyrosine-oxytocin (Swedish patent 7713/70 publication No 353,531), and [1-deaminopenicillamine,2-O-methyltyrosine]oxytocin (J. Lowbridge et al, Journal of Medicinal Chemistry 22, (1979), pp 565–569).

It should be observed that these earlier studies have been effected solely on rats. As far as is known, no one has studied oxytocin derivatives on human material with regard to inhibitory effects. Making the present invention, we have now tested and found inhibitory effects of peptides on uterine musculature from a pregnant and a non-pregnant woman, respectively. It was remarkable that the oxytocin derivatives according to the invention could also inhibit vasopressin induced contractions when experiments were made with tissue from a non-pregnant woman. Of particularly great interest is that the present oxytocin derivatives inhibit the spontaneous contraction pattern of the uterus, which has never before been reported.

Hiterto there has not been any medicine devoid of secondary effects that has been capable of counteracting excessive muscle contractions in the uterus. Therapeutants known today which have this effect, are β-receptor-agonists, prostaglandin synthesis inhibitors, calcium antagonists and ethanol. All of these agents have non-specific effects and thus produce secondary effects.

The compounds according to the present invention therefore are of considerable clinical interest in cases of premature labour or excessive spasms in the uterus in connection with delivery and menstruation (partus praematurus, dysmenorrhoea).

One object of the present invention is to provide an oxytocin derivative of the formula

wherein Mpa is a 3-mercaptopropionyl residue and X is an alkyl group having 2–4 carbon atoms which substitute the hydrogen in the hydroxyl group of the tyrosine.

In the oxytocin derivative of the above formula X may be ethyl.

Another object of the invention is to provide a pharmaceutical composition comprising at least one oxytocin derivative as active ingredient in combination with pharmaceutically acceptable additives and/or diluents.

Still another object of the invention is to provide a pharmaceutical composition comprising a physiological saline solution as pharmaceutically acceptable diluent and mannitol as additive.

Yet another object of the invention is to use oxytocin derivatives in the production of medicines.

A further object of the invention is to provide a method of counteracting excessive muscle contractions of the uterus, comprising administering a pharmaceutical composition which contains an effective amount of at least one oxytocin derivative.

A still further object of the invention is to provide a method in which the effective amount of oxytocin derivative is 5–25 μg.

The oxytocin derivatives according to the present invention may preferably be administered dissolve in physiological saline solution by injection, infusion or inhalation.

The compounds according to the invention can be produced in analogy with processes well-known within the art. In the following Examples a representative compound according to the invention, viz. 1-deamino-2-O-ethyltyrosine-oxytocin, has been produced in conformity with what has been described by Law, H. B. & Du Vigneaud, V. in Journal of the American Chemical Society 82, (1960) 4579-4581, Zhuze, A. L., Jost, K., Kasafírek, E. & Rudinger, J. in Collection of Czechoslovak Chemical Communications 29, (1963), 2648-2662, and modified by Larsson, L.-E., Lindeberg, G., Melin, P. & Pliska, V. in Journal of Medicinal Chemistry 21, (1978), 352–356. These works are hereby incorporated by reference.

In the following Example use has been made of the following abbreviations:
Cbz=carbobenzyloxy group
Bzl=benzyl group
Mpa=2-mercaptopropionyl group
ONp=p-nitrophenylester group
MDF=dimethyl formamide

EXAMPLE 1.0 g Cbz-Ile-Gln-Asn-Cys-Bzl-Pro-Leu-Gly-NH$_2$ (from Ferring AB, Malmö, Sweden) was deblocked with 30 ml HBr and 20 ml HOAc and coupled for 48 h with 477 mg Cbz-Tyr(ethyl)-ONp in 7 ml DMF, in the presence of N-ethyldiisopropylamine. The product was precipitated with water. The precipitate was washed with water, ethanol, acetone and ethyl acetate and recrystallized from acetic acid/ethanol. Thus, 0.93 g (79%) Cbz-Tyr(ethyl)-Ile-Gln-Asn-Cys(Bzl)-Pro-Leu-Gly-NH$_2$, was obtained, which displayed a homogeneous thin layer in the systems n-butanol/acetic acid/water 4:1:1 and n-butanol/acetic acid/pyridine/water 15:3:10:6.

0.44 g of this compound was deblocked as described above and coupled with 0.12 g Mpa(Bzl)-ONp. This yielded 0.337 g (75%) Mpa(Bzl)-Tyr(ethyl)-Ile-Gln-Asn-Cys(Bzl)-Pro-Leu-Gly-NH$_2$ which displayed a homogeneous thin layer in the same system as above.

0.3 g of the last-mentioned compound was deblocked with sodium in 400 ml condensed, sodium-dried ammonia and dissolved in 350 ml water (acidified with acetic acid). This yielded a turbid solution which was filtered and extracted with ether (2×100 ml). pH was adjusted at 7.4 and 0.01 M K$_3$Fe(CN)$_6$ was added (15 ml). The mixture was agitated for 20 minutes and acidified, whereupon it was decolourized on chloride ion exchanger Dowex-50 ® (from Dow Chemical Co, The Midland, Michigan, USA) and freeze-dried.

The freeze-dried material was desalted on Sephadex G-15 ® (1.4×140 cm column) in 50% (vol/vol) acetic acid/water. The main fraction was diluted with water and freeze-dried. The Sephadex materials are dextran gels supplied by Pharmacia Fine Chemicals AB, Uppsala, Sweden.

The main component was gelfiltered on Sephadex G-25 ® (Superfine) (1.6×90 cm) in 0.05 M ammonium acetate, pH 5.0. The main fraction was flushed and freeze-dried.

The remainder was dissolved in n-butanol/acetic acid/water 4:1:1 and chromatographed on Sephadex LH-20 ® in this system. The material was evaporated, dissolved in water and freeze-dried.

Said freeze-dried material was finally gelfiltered once more in the same way as described above.

Thus, 8 mg 1-deamino-2-O-ethyltyrosine-oxytocin was obtained. The purity of the product was checked by thin layer chromatography on cellulose plates in the systems n-butanol/acetic acid/water 4:1:5 (upper phase) and n-butanol/acetic acid/pyridine/water 15:3:10:12.

The product was also homogeneous on HPLC column μ-Bondapak C-18 in 45% ethanol and 55% 5 mM trifluoroacetic acid in water. Said column was supplied by Waters Associates, Inc., Millford, Mass., USA. Amino acid analysis: Asp: 1.02, Glu: 1.03, Gly: 0.98, Ile: 0.97, Leu: 0.99, Tyr: 0.75; Tyr(ethyl) does not provide a complete hydrolysis to Tyr.

The known compounds 2-O-methyltyrosine-oxytocin and 2-O-ethyltyrosine-oxytocin and a representative compound according to the invention, viz. 1-deamino-(2-O-ethyltyrosine)-oxytocin, was examined with regard to uterotonic potency on isolated rat uterus with use of oxytocin as standard. The antagonistic properties of the compounds were also evaluated with the aid of said preparation, but also in vivo with use of oxytocin as agonist. Moreover, the inhibition of oxytocin effect on isolated human myometrium was examined.

In vitro experiments

Sprague Dawley rats (body weight approximately 250 g) in natural estrous were selected by vaginal smears. An approximately 20 mm long segment was cut from the middle of a uterine horn and mounted in an organ bath containing 10 ml of a modified Locke's solution of the following composition (mM:NaCl 153, KCl 5.63, CaCl$_2$ 0.541, NaHCO$_3$ 5.95 and glucose 2.78). The solution was gassed with 5% CO$_2$ in oxygen at 30° C. The uterine contractions were allowed to stabilize for 30 minutes. Contractions were recorded isometrically at a resting tension of 1.5 g using Grass force transducers (Ft. 03). Antagonistic potency of the analogues was calculated as pA$_2$ values (Rudinger, J. & Krejci, I. Experientia 18, (1962), 585–588). pA$_2$ is a measure of the inhibitory property of the peptide and was defined by Schild (Schild, H. O., British Journal of Pharmacology, 2, (1947), 189–206) as the negative logarithm of the molar concentration of an antagonist which reduces the effect of a dose of agonist to that of half the dose.

From 17 patients undergoing caesarean section (week 37–40) a transverse segment of uterine tissue was excised from the isthmic part of the uterus. Tissue pieces were also excised from the ventral side of the uterus of 21 non-pregnant women in fertile age undergoing hysterectomy. The tissue pieces were immediately placed in Krebs-Ringer solution (mM: NaCl 118, KCl 4.6, CaCl$_2$ 2.5, MgSO$_4$ 1.15, NaHCO$_3$ 24.9, KH$_2$PO$_4$ 1.15 and glucose 5.5) at 0° C. and used within two hours after the operation. Segments pieces 25×3×3 mm large were mounted in an organ bath containing 10 ml Krebs-Ringer solution at 37° C. and gassed with 5% CO$_2$ in oxygen. After an adaptation period of 30 minutes contractions were isometrically recorded at a resting tension of 1.25 g. In experiments involving pregnant women use was made of oxytocin (0.013–1.3 μg/ml) as an agonist. Lysinevasopressin (0.07–1.3 μg/ml) was used as an agonist where non-pregnant tissue was tested. A suitable dose of agonist was selected, which gave an effect corresponding to approximately 40% of the maximum effect. The antagonist was used in a concentration of 0.33–1.32 μg/ml. The response of the myometrial tissue to the agonist was always checked at the start and at the end of an experiment. When the effects of the peptide had faded away the tissue was washed with 3×10 ml of buffer solution. The inhibitory effect of the antagonist was measured by planimetry, for 15 minutes after the addition of the peptide, of the total surface of the curve recorded. Inhibition was expressed as a percentage of the effect obtained with the agonist alone.

In vivo experiments

Sprague Dawley rats (250 g) in natural estrous were anaesthetized with Inactin (0.5 mg/100 g body weight i.p.). Myometrial activity was recorded by means of a catheter fixed in the uterine cavity and filled with modified Locke's solution. The catheter was connected to a Statham P23d transducer and contractions were recorded on a Grass polygraph (model 7D). Oxytocin was infused intravenously (0.05 μg/min/100 g body weight). When a regular contraction pattern had been obtained the antagonist (0.8–8.0 μg/100 g body weight) was administered intravenously in a volume of 0.2 ml. The recorded curve was integrated over 10 minute intervals immediately before and after injection of the antagonist.

Results

By the rat in vitro experiments it could be established that 2-O-methyltyrosine-oxytocin and 2-O-ethyltyrosine-oxytocin displayed uterotonic potency of the order 1-2 IU/mg. On the other hand, the respective 1-deaminated analogues had no measurable anagonistic activity.

All of the derivatives examined caused a competitive inhibition of the oxytocin effect, as judged by their $pA_2$ values according to the Table below. (It may be mentioned in this context that $pA_2$ values obtained at different laboratories are not comparable because the test conditions are never equivalent.)

TABLE

Oxytocin derivative was tested with regard to antagonistic activity on rat uterus preparations (in vitro) stimulated with oxytocin.

| Derivative | $pA_2$ (average ± average error) | Number of experiments |
|---|---|---|
| 2-O—methyltyrosine-oxytocin | 6.68 ± 0.12 | (12) |
| 2-O—ethyltyrosine-oxytocin | 7.13 ± 0.09 | (8) |
| 1-deamino-2-O—ethyltyrosine-oxytocin | 7.19 ± 0.10 | (5) |

The above Table shows that the tested compounds have similar and rather high $pA_2$ values. It is obvious that the deamination at position 1 of the peptide chain does not significantly change the inhibitor activity in tests on isolated rat uterine preparations, but on the other hand—as has been mentioned above—causes disappearance of the agonist effect.

It appeared from the in vitro experiments on uterine tissue from pregnant women that the oxytocin derivative according to the invention heavily inhibited oxytocin induced contractions. Such an effect was attained at a dose ratio, antagonist: agonist, of 3 to 5, i.e. inhibition of the oxytocin stimulated contractions occurred when the concentration of the inhibitor was 3 to 5 times greater compared to oxytocin. The inhibition mainly appeared as a decrease of the muscular tonus and contraction frequency of the uterus. A complete blocking of the oxytocin and vasopressin effects on a pregnant and non-pregnant human uterus, respectively occurred at a dose of the oxytocin derivative which was approximately 5 times higher than the agonist dose. With 2-O-ethyltyrosine-oxytocin a significant inhibition was obtained, which was however considerably lower than with use of the compound according to the invention. The effects were reversible. It was stated for the known compound $N^\alpha$-acetyl-2-O-methyltyrosine-oxytocin that a complete inhibition of oxytocin occurred at a quantity ratio of 15:1 to 20:1, thus at a many times higher concentration than that of the present invention.

At the rat in vivo experiments with the present oxytocin derivative, 2-O-methyltyrosine-oxytocin and 2-O-ethyltyrosine-oxytocin there occurred a dose dependent reversible inhibition of the increase of the strength of the uterine contractions which had been caused by infusion of oxytocin (0.05 µg/min/100 g body weight).

It could be established that the analogue used was considerably more active as inhibitor compared to the two known analogues. It was remarkable that the oxytocin derivative in a dose of 2 µg could completely block the uterine contraction pattern (contrary to 2-O-ethyltyrosine-oxytocin and 2-O-methyltyrosine-oxytocin which lack this ability), thus not only the contractions initiated by oxytocin but also the spontaneous muscular activity of the organ. This latter observation in all probability is not coupled to any effect on the circulation since the analogue in so high does as 30 µg intravenously had no effect at all on the blood pressure.

This result is extremely surprising considering that one has not earlier been able to inhibit the spontaneous contractions of the uterus. In the above mentioned Swedish patent 7713/70 it has been expressly stated that $N^\alpha$-acetyl-2-O-methyltyrosine-oxytocin has no effect on the spontaneous uterine function.

Clinical experiments on four voluntary women

The effect of 1-deamino-(2-O-ethyltyrosine)-oxytocin (dEtOx) on the uterine contraction pattern of four women was studied according to the method described by Åkerlund M., Bengtson L. P. and Ulmsten U. in "Recording of myometric action in the non-pregnant human uterus by a micro transducer". Acta Obstet. Gynecol. Scand., Vol 57, pp 429–433, 1978, which is here incorporated by reference.

In four different experiments on three normal women under early menstruation the pressure in the uterus was continuously recorded by a micro transducer (PC 350, Millar Instruments, Houston, USA) fixed in the uterine cavity. The women was continuously infused with lysine vasopressin, 0.08 µg/min, for stimulation of the muscular contractions of the uterus. Then a single dose of 5-25 µg dEtOx was administered intravenously to each woman. The amplitude and frequency of the uterine contraction pattern were inhibited to on the whole the same values as before the lycine vasopressin infusion. This effect varied between the different women and lasted for 45-180 minutes.

A single injection of dEtOx was tested on a woman suffering from a severe spontaneous menstrual pain. Earlier studies had shown an elevated plasma concentration of vasopressin in women suffering from such pains. (Akerlund M, Forsling M, Strömberg P., "Primary dysmenorrhoea and vasopressin", Br. J. Obstet. Gynecol. 86:485, 1979, and Strömberg P., Forsling M., Akerlund M. "Vasopressin levels in women with primary dysmenorrhoea before and after treatment with a prostaglandin synthesis inhibitor", Obstet. Gynecol., in press.) After intravenous supply of 10 µg dEtOx the woman felt a pronounced alleviation of the pain simultaneously as her normal colouring returned and she looked less harassed.

Preparation of pharmaceutical composition 1 mg oxytocin derivative and 10 mg mannitol were freeze-dried and put into an ampoule which was sealed. For intravenous administration the ampoule content was diluted with isotonic saline solution to a concentration of 10 µg oxytocin derivative per 1 ml solution.

I claim:

1. Oxytocin derivative of the formula

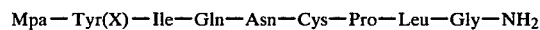

Mpa—Tyr(X)—Ile—Gln—Asn—Cys—Pro—Leu—Gly—NH₂ wherein Mpa is a 3-mercaptopropionyl residue and X is an alkyl group having 2-4 carbon atoms which substitute the hydrogen in the hydroxyl group of the tyrosine.

2. Oxytocin derivative as claimed in claim 1, wherein X is ethyl.

3. Pharmaceutical composition for counteracting excessive muscular contractions of the uterus comprising at least one derivative according to claim 1 as an active ingredient in combination with a pharmaceutically acceptable additive and/or diluent.

4. Pharmaceutical composition as claimed in claim 3 comprising a physiological saline solution as pharmaceutically acceptable diluent and mannitol as additive.

5. A method of counteracting excessive muscular contractions of the uterus, wherein a pharmaceutical composition containing an effective amount of at least one derivative according to claim 1, is administered.

6. A method as claimed in claim 5 wherein the effective amount is 5–25 μg.

7. A pharmaceutical composition as defined in claim 3, wherein X is ethyl.

8. A pharmaceutical composition as claimed in claim 3, wherein a physiological saline solution is present as a pharmaceutically acceptable diluent.

9. A method of counteracting excessive muscular contractions of the uterus, wherein a pharmaceutical composition containing an effective amount of at least one derivative according to claim 1 is administered.

10. A method as defined in claim 9 wherein X is ethyl.

11. A pharmaceutical composition as claimed in claim 3, wherein the active ingredient is present in the amount of 0.8–8.0 μg/100 g body weight.

12. An intravenous solution containing as an active ingredient an oxytocin derivative of claim 1 in a physiological saline solution.

13. The composition of claim 3, wherein the active ingredient is in a concentration of 10 micrograms per ml of solution.

14. A solution suitable for inhalation comprising an oxytocin derivative as defined in claim 1 dissolved in physiological saline solution.

* * * * *